US009604040B1

(12) United States Patent
Woolley et al.

(10) Patent No.: US 9,604,040 B1
(45) Date of Patent: *Mar. 28, 2017

(54) SYSTEM AND METHODS FOR PERFORMING SPINAL FUSION SURGERY

(71) Applicant: NuVasive, Inc., San Diego, CA (US)

(72) Inventors: Troy B. Woolley, Erie, CO (US);
Nathan Lovell, Oceanside, CA (US)

(73) Assignee: NUVASIVE, INC., San Diego, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 14/532,316

(22) Filed: Nov. 4, 2014

Related U.S. Application Data

(63) Continuation of application No. 13/831,711, filed on Mar. 15, 2013, now Pat. No. 8,876,851, which is a continuation of application No. 12/580,214, filed on Oct. 15, 2009, now abandoned.

(60) Provisional application No. 61/105,791, filed on Oct. 15, 2008.

(51) Int. Cl.
*A61M 29/00* (2006.01)
*A61B 17/00* (2006.01)
*A61B 17/02* (2006.01)

(52) U.S. Cl.
CPC ....... *A61M 29/00* (2013.01); *A61B 17/00234* (2013.01); *A61B 17/025* (2013.01); *A61B 17/0218* (2013.01); *A61B 2017/00261* (2013.01); *A61B 2017/0256* (2013.01); *A61B 2017/0262* (2013.01)

(58) Field of Classification Search
CPC .............................. A61M 29/00; A61B 17/00
USPC .............. 600/201–246; 606/86 A, 105, 198;
623/17.11–17.16
See application file for complete search history.

(56) References Cited

U.S. PATENT DOCUMENTS

| 208,227 A | 9/1878 | Dorr |
| 972,983 A | 10/1910 | Arthur |
| 1,328,624 A | 1/1920 | Graham |
| 4,545,374 A | 10/1985 | Jacobson |
| 4,573,448 A | 3/1986 | Kambin |
| 5,007,902 A | 4/1991 | Witt |
| 5,171,279 A | 12/1992 | Mathews |
| 5,295,994 A | 3/1994 | Bonutti |
| 5,312,417 A | 5/1994 | Wilk |
| 5,331,975 A | 7/1994 | Bonutti |
| 5,342,384 A | 8/1994 | Sugarbaker |
| 5,378,241 A | 1/1995 | Haindl |
| 5,395,317 A | 3/1995 | Kambin |

(Continued)

FOREIGN PATENT DOCUMENTS

| JP | 11290337 | 10/1999 |
| KR | 20100123083 | 11/2010 |

(Continued)

*Primary Examiner* — Christopher Beccia
(74) *Attorney, Agent, or Firm* — Bardley Arant Boult Cummings LLP

(57) ABSTRACT

A system and method for performing spine surgery, including a tissue distraction assembly. The tissue distraction assembly includes an initial dilator, a secondary dilator, a first expander, and a second expander. The tissue distraction assembly is provided with an overall generally oblong shape. The tissue distraction assembly provides for asymmetrical tissue distraction in a single direction.

14 Claims, 12 Drawing Sheets

(56) References Cited

U.S. PATENT DOCUMENTS

| | | | |
|---|---|---|---|
| 5,423,825 A * | 6/1995 | Levine | A61B 17/1604 29/275 |
| 5,509,893 A | 4/1996 | Pracas | |
| 5,514,153 A | 5/1996 | Bonutti | |
| 5,599,279 A | 2/1997 | Slotman | |
| 5,707,359 A | 1/1998 | Bufalini | |
| 5,762,629 A | 6/1998 | Kambin | |
| 5,792,044 A | 8/1998 | Foley | |
| 5,814,073 A | 9/1998 | Bonutti | |
| 5,817,071 A | 10/1998 | Dewindt | |
| 5,888,196 A | 3/1999 | Bonutti | |
| 5,902,231 A | 5/1999 | Foley | |
| 5,910,134 A | 6/1999 | Fussman | |
| 5,976,146 A | 11/1999 | Ogawa | |
| 6,007,487 A | 12/1999 | Foley | |
| 6,146,371 A | 11/2000 | Dewindt | |
| 6,152,871 A | 11/2000 | Foley | |
| 6,161,047 A | 12/2000 | King | |
| 6,206,826 B1 | 3/2001 | Mathews | |
| 6,217,509 B1 | 4/2001 | Foley | |
| 6,217,527 B1 | 4/2001 | Selmon | |
| 6,221,049 B1 | 4/2001 | Selmon | |
| 6,224,599 B1 * | 5/2001 | Baynham | A61B 17/025 606/79 |
| 6,231,546 B1 | 5/2001 | Milo | |
| 6,270,505 B1 | 8/2001 | Yoshida | |
| 6,277,094 B1 | 8/2001 | Schenedel | |
| 6,292,701 B1 | 9/2001 | Prass | |
| 6,325,764 B1 | 12/2001 | Griffith | |
| 6,395,007 B1 | 5/2002 | Bhatnagar | |
| 6,425,859 B1 | 7/2002 | Foley | |
| 6,447,484 B1 | 9/2002 | Briscoe | |
| 6,506,151 B2 | 1/2003 | Estes | |
| 6,514,217 B1 | 2/2003 | Selmon | |
| 6,520,907 B1 | 2/2003 | Foley | |
| 6,535,759 B1 | 3/2003 | Epstein | |
| 6,564,078 B1 | 5/2003 | Marino | |
| 6,641,582 B1 * | 11/2003 | Hanson | A61B 17/1671 606/79 |
| 6,641,613 B2 | 11/2003 | Sennett | |
| 6,645,194 B2 | 11/2003 | Briscoe | |
| 6,679,833 B2 | 1/2004 | Smith | |
| 6,719,692 B2 | 4/2004 | Kleffner | |
| 6,847,849 B2 | 1/2005 | Mamo | |
| 6,855,105 B2 | 2/2005 | Jackson | |
| 6,916,330 B2 | 7/2005 | Simonson | |
| 6,926,728 B2 | 8/2005 | Zucherman | |
| 6,929,606 B2 | 8/2005 | Ritland | |
| 7,008,431 B2 | 3/2006 | Simonson | |
| 7,074,226 B2 | 7/2006 | Roehm | |
| 7,083,625 B2 | 8/2006 | Berry | |
| 7,198,598 B2 | 4/2007 | Smith | |
| 7,207,949 B2 | 4/2007 | Miles | |
| 7,217,246 B1 | 5/2007 | Stone | |
| 7,226,451 B2 | 6/2007 | Shluzas | |
| 7,276,055 B2 | 10/2007 | Dewindt | |
| 7,311,719 B2 | 12/2007 | Bonutti | |
| 7,320,688 B2 | 1/2008 | Foley | |
| 7,470,236 B1 | 12/2008 | Kelleher | |
| 7,569,061 B2 | 8/2009 | Colleran | |
| 7,582,058 B1 | 9/2009 | Miles | |
| 7,588,588 B2 | 9/2009 | Spitler | |
| 7,594,888 B2 | 9/2009 | Raymond | |
| 7,608,094 B2 | 10/2009 | Falahee | |
| 7,618,431 B2 | 11/2009 | Roehm, III | |
| 7,708,761 B2 | 5/2010 | Petersen | |
| 7,837,713 B2 | 11/2010 | Petersen | |
| 7,959,564 B2 | 6/2011 | Ritland | |
| 7,981,029 B2 | 7/2011 | Branch | |
| 7,993,378 B2 | 8/2011 | Foley et al. | |
| 8,043,212 B1 * | 10/2011 | Bae | A61B 17/0218 600/215 |
| 8,075,591 B2 | 12/2011 | Ludwig et al. | |
| 8,142,507 B2 | 3/2012 | McGuckin, Jr. | |
| 2001/0056280 A1 | 12/2001 | Underwood | |
| 2002/0010392 A1 | 1/2002 | Desai | |
| 2003/0139648 A1 | 7/2003 | Foley | |
| 2004/0106999 A1 | 6/2004 | Mathews | |
| 2004/0181231 A1 | 9/2004 | Emstad | |
| 2005/0004593 A1 | 1/2005 | Simonson | |
| 2006/0052669 A1 | 3/2006 | Hart | |
| 2006/0052828 A1 | 3/2006 | Kim | |
| 2006/0253132 A1 | 11/2006 | Evans et al. | |
| 2007/0066977 A1 | 3/2007 | Assell | |
| 2007/0083161 A1 | 4/2007 | Briscoe | |
| 2007/0233155 A1 * | 10/2007 | Lovell | A61B 17/7076 606/104 |
| 2008/0077152 A1 | 3/2008 | McClintock et al. | |
| 2008/0091269 A1 | 4/2008 | Zipnick et al. | |
| 2009/0270902 A1 | 10/2009 | Assell et al. | |
| 2010/0022844 A1 | 1/2010 | Mangiardi | |
| 2010/0081885 A1 | 4/2010 | Wing et al. | |
| 2010/0106194 A1 | 4/2010 | Bonutti et al. | |
| 2010/0114147 A1 | 5/2010 | Biyani | |
| 2010/0222824 A1 | 9/2010 | Simonson | |
| 2010/0222829 A1 | 9/2010 | Petersen | |
| 2010/0280555 A1 | 11/2010 | Aflatoon et al. | |
| 2010/0331891 A1 | 12/2010 | Culbert et al. | |
| 2011/0077685 A1 | 3/2011 | Carls et al. | |
| 2011/0144687 A1 | 6/2011 | Kleiner | |
| 2011/0208226 A1 | 8/2011 | Fatone | |

FOREIGN PATENT DOCUMENTS

| | | |
|---|---|---|
| WO | WO 97/40878 | 11/1997 |
| WO | WO 2011/044484 | 4/2011 |

* cited by examiner

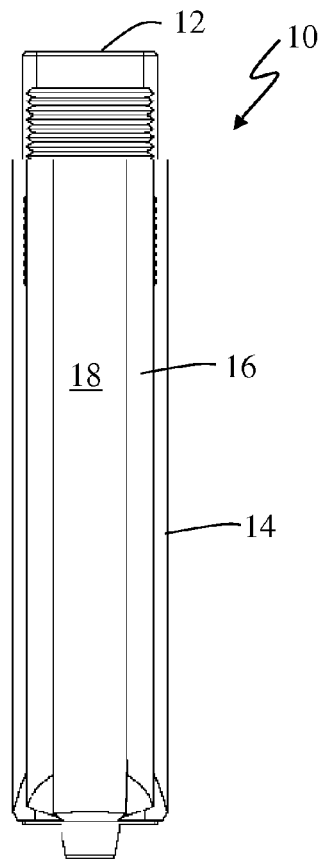
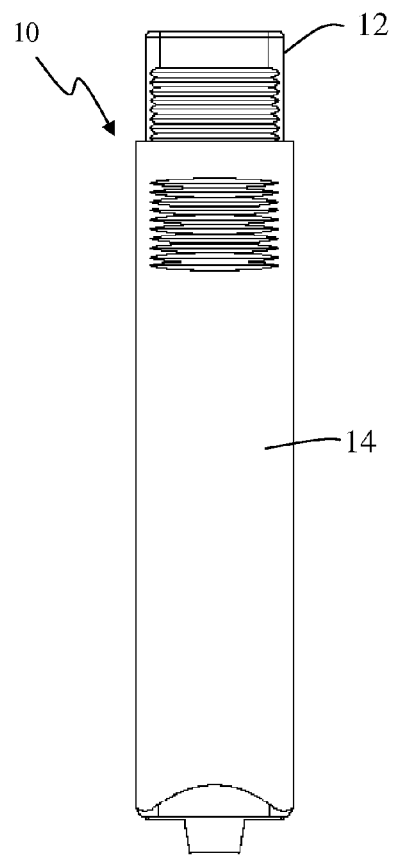
FIG. 3          FIG. 4
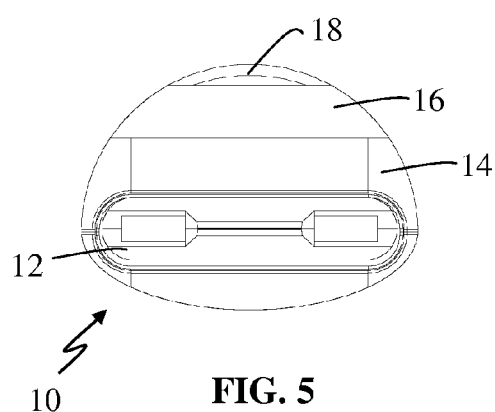
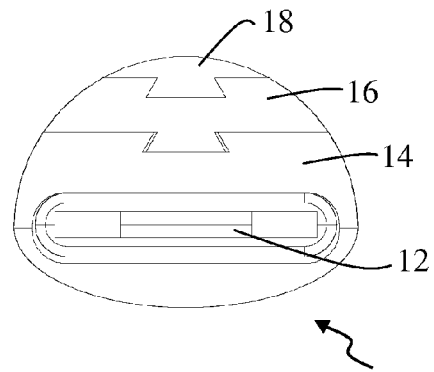
FIG. 5          FIG. 6

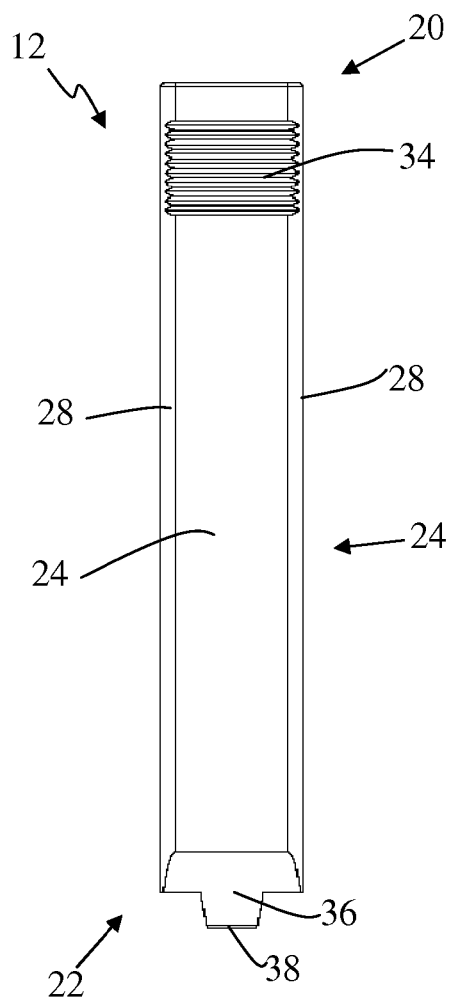
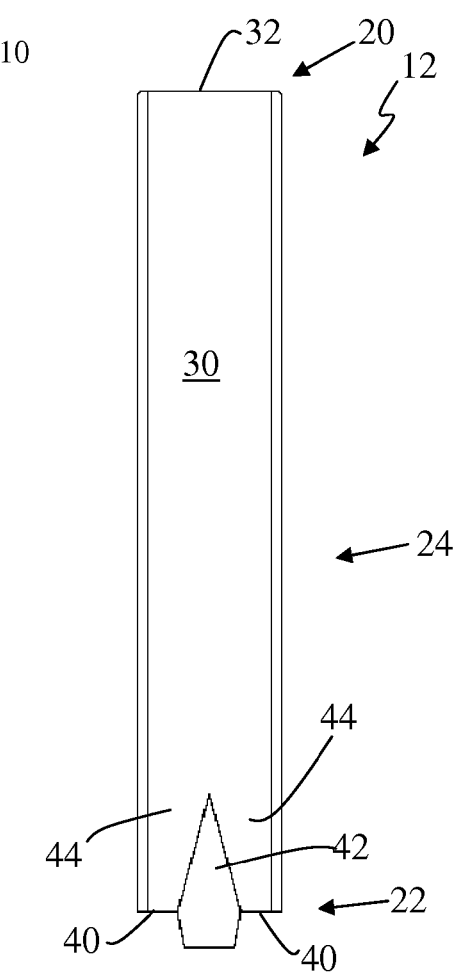
FIG. 10  FIG. 11
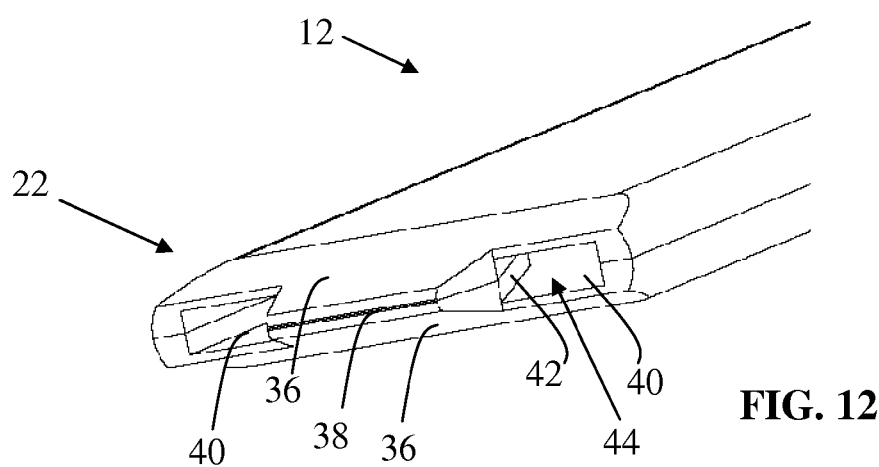
FIG. 12

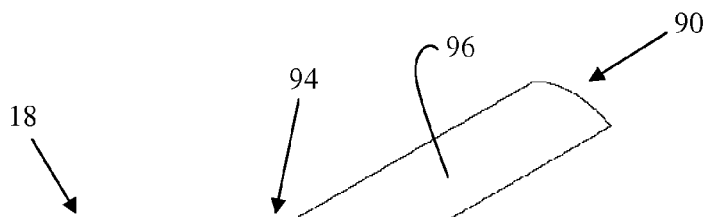
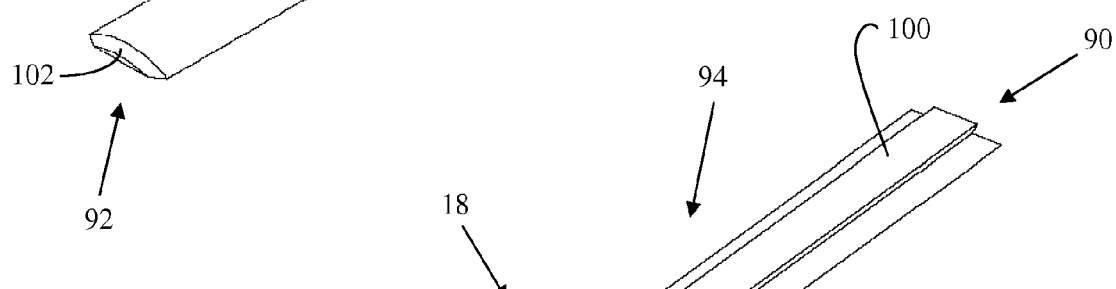
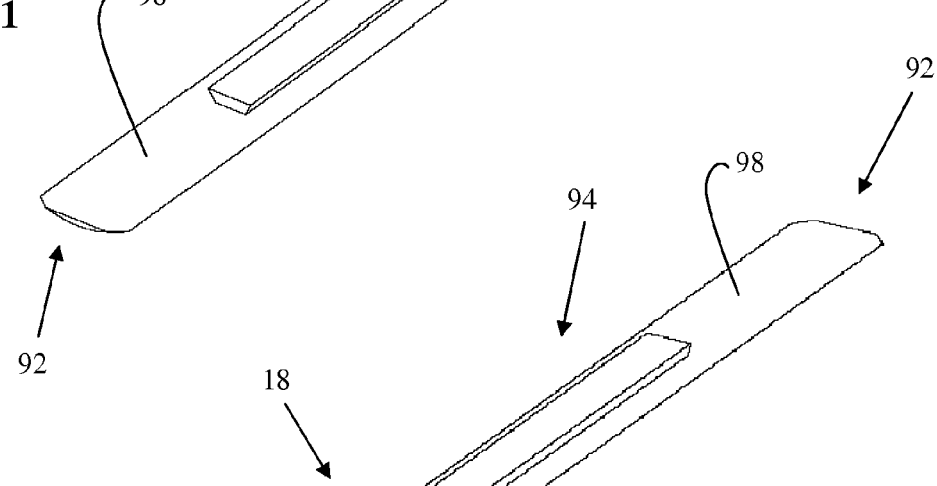
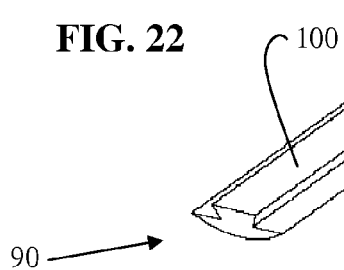

SYSTEM AND METHODS FOR PERFORMING SPINAL FUSION SURGERY

CROSS-REFERENCES TO RELATED APPLICATIONS

The present application is a continuation of U.S. application Ser. No. 13/831,711, filed Mar. 15, 2013, now U.S. Pat. No. 8,876,851, which is a continuation of U.S. application Ser. No. 12/580,214, filed Oct. 15, 2009, which claims the benefit of priority under 35 USC §119(e) from U.S. Provisional Patent Application No. 61/105,791, filed Oct. 15, 2008, the entire contents of which are incorporated by reference into this disclosure.

FIELD

The present application describes systems and methods used for dilating tissue during surgery.

BACKGROUND

Spinal discs serve to cushion and stabilize the spine in addition to distributing stress and damping cyclic loads. The discs may become damaged due to injury or age and symptoms of a damaged disc may include severe pain, numbness or muscle weakness. Surgical intervention is often required to alleviate the symptoms of damaged discs. For example, fusion is one method of reducing the magnitude of the symptoms of damaged spinal discs. The primary goals of fusion procedures are to provide stability between the vertebrae on either side of the damaged disc and to promote natural fusion of those adjacent vertebrae. In order to intervene, the surgeon must access the spine through layers of body.

SUMMARY OF THE INVENTION

The present describes an improved tissue distraction assembly. The tissue distraction assembly includes a variety of sub-components dimensioned to allow for sequential dilation of a surgical tissue site in order to establish an operative corridor through a patient's skin to a surgical target site. By way of example only, the surgical target site referred to herein throughout is an intervertebral disc space situated between two adjacent vertebrae. Although particularly suited for use in lumbar spine fixation, it will be readily appreciated by those skilled in the art that the surgical fixation system of the present invention may be employed in any number of suitable orthopedic fixation approaches and procedures, including but not limited to anterior, posterior, lateral, antero-lateral, postero-lateral, cervical spine fixation, thoracic spine fixation, as well as any non-spine fixation application such as bone fracture treatment.

The tissue distraction assembly includes an initial dilator, a secondary dilator, a first expander, and a second expander. The tissue distraction assembly is provided with an overall generally oblong shape as opposed to a generally circular shape characterizing many of the sequential dilation systems currently available. This oblong shape serves to provide an initial distraction corridor spanning a target disc space, allowing the placement of pedicle screws at adjacent levels without additional tissue retraction. As will be explained in greater detail below, the first and second expanders function to bias the distraction corridor in one direction. By way of example only, based on the preferred positioning of the tissue distraction system during use, the distraction corridor is biased medially (e.g. toward the patient's longitudinal midline).

The initial dilator has a proximal portion, a distal portion, and an elongated body extending therebetween. The initial dilator is formed from a pair of generally planar panels connected by generally curved sides, such that the initial dilator has a generally oblong cross-section. The initial dilator further has a lumen extending through the dilator from the proximal portion to the distal portion. The proximal portion further includes a proximal opening of the lumen, and a plurality of friction elements provided to enhance user control of the instrument. By way of example only, the friction elements are provided as a plurality of ridges, however any suitable friction-inducing material and/or feature may be employed without departing from the scope of the present invention. The distal portion includes a lead element having a leading edge extending along the lead element. Lead element is tapered in a distal direction from the planar panels to the leading edge to enable the lead element to advance through tissue (e.g. muscle tissue) without requiring severing or removal of that tissue. The distal portion further includes a pair of distal openings positioned on either side of lead element. Distal openings represent the distal terminus of the lumen.

The lumen extends through the initial dilator from the proximal opening to the distal openings. The distal portion of the initial dilator further includes a wedge member extending proximally into the lumen, effectively bifurcating the lumen into a pair of distal channels leading to the distal openings. The distal channels function to guide relevant instrumentation (e.g. K-wires) into the proper positioning within the surgical target site.

The secondary dilator has a proximal portion, a distal portion, and an elongated body extending therebetween. The secondary dilator includes a first side, a second side, and a pair of generally curved lateral sides. The first side comprises a generally planar surface having an elongated recess extending from the end of the proximal portion substantially the length of the elongated body and terminating near the distal portion. The second side comprises a surface having a generally convex curvature. The convex surface of the second side represents one boundary of the distraction corridor because any further distraction at this point will be due to the extensions as explained in further detail below. Both the first and second sides are provided with a plurality of friction elements at the proximal portion provided to enhance user control of the instrument. By way of example only, the friction elements are provided as a plurality of ridges, however any suitable friction-inducing material and/or feature may be employed without departing from the scope of the present invention. The secondary dilator further includes a lumen extending through the dilator from the proximal portion to the distal portion. The lumen has an oblong cross-section, and is sized and dimensioned to slideably enagage the initial dilator. The lumen further includes a proximal opening and a distal opening.

The distal portion further includes a pair of generally planar surfaces that are sloped or tapered from the first and second sides to the distal opening of the lumen. During tissue distraction, as the secondary dilator is being advanced over the initial dilator to expand the operative corridor, the tapered surfaces function to urge the body tissue around the path of the dilator. When the secondary dilator has been fully inserted, the initial dilator may be removed if desired, and the secondary dilator 14 may act as a stand-alone cannula.

In some instances, it may be desirable to enlarge the distraction corridor further. To achieve that end, further sequential dilators may be provided without departing from the scope of the present invention. Additionally, one or more extensions may be provided to slideably engage with the secondary dilator and thereby expand the distraction corridor. The tissue distraction system may be configured such that extensions are provided on one or more sides of the secondary dilator, to achieve a distraction corridor of any customizable shape. By way of example only, the tissue distraction assembly described herein is configured to include expanders on only one side of the secondary dilator, creating a biased corridor configuration.

The first expander includes a proximal end portion, a distal end portion, and an elongated body extending therebetween. The first expander further includes a first side comprising a generally planar surface and a second side comprising a generally planar surface opposite the first side. The first side includes an elongated recess extending from the proximal end portion substantially the length of the body portion and terminates near the distal end portion. The second side includes an elongated raised protrusion extending from the proximal end portion substantially the length of the body portion and terminates near the distal end portion. The protrusion is sized and dimensioned to slideably engage the elongated recess of the secondary dilator. Thus, the protrusion and recess will have complementary shapes and sizes. Any such shape is possible, for example including but not limited to the mortise and tenon interfaces shown in the figures. The distal end portion further includes a distal tapered surface that slopes in a distal direction from the first surface until it forms an edge with the second surface. The first expander further includes a pair of lateral tapered surfaces that slopes in a lateral direction from the first surface until it forms an edge with the second surface. The lateral tapered surfaces extend along the length of the body portion. Both the distal tapered surface and lateral tapered surfaces function to urge the body tissue around the path of the first expander during tissue distraction, as the first expander is being advanced over the initial dilator to expand the operative corridor.

The second expander includes a proximal end portion, a distal end portion, and an elongated body extending therebetween. The second expander further includes a first side comprising a generally convex surface and a second side comprising a generally planar surface opposite the first side. The second side includes an elongated raised protrusion extending from the proximal end portion substantially the length of the body portion and terminates near the distal end portion. The protrusion is sized and dimensioned to slideably engage the elongated recess of the first expander. Thus, the protrusion and recess will have complementary shapes and sizes. Any such shape is possible, for example including but not limited to the mortise and tenon interfaces shown in the figures. The distal end portion further includes a distal tapered surface that slopes in a distal direction from the first surface until it forms an edge with the second surface. The distal tapered surface functions to urge the body tissue around the path of the second expander during tissue distraction, as the second expander is being advanced over the first expander to expand the operative corridor.

The first step in the distraction process is to typically run a guide to the target site. In this instance, for example the surgeon would advance a pair of K-wires to the relevant locations (i.e. pedicles) involved in the procedure in order to guide the proper placement of the dilators. After an initial incision is made within the skin to allow passage of the dilators, the initial dilator is advanced along the K-wires such that one K-wire is in each distal channel of the lumen. Once the initial dilator has been satisfactorily placed, the secondary dilator is advanced over the top of the initial dilator. If further distraction is required (e.g. medial distraction), first and second expanders may be employed.

Once the distraction corridor has been created, a tissue retractor may be advanced to the spine over the distraction assembly (not shown). The distraction assembly may be removed and the retractor may be operated to expand to establish an operative corridor. With the operative corridor established, the surgeon may proceed with the desired procedure, for example, a transforaminal lumbar interbody fusion (TLIF) spinal procedure. This procedure continues with a facetectomy in which at least a portion of the facet joint is removed, allowing access to the intervertebral disc space. The disc space is prepared using techniques generally known in the art, including disc brushes, scrapers, etc. The interbody implant is then inserted into the cleaned out disc space. The retractor may then be removed from the patient, closing the operative corridor. The surgeon will then close the operative wound, completing the procedure.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 3 is a front plan view of the tissue distraction assembly of FIG. 1;

FIG. 4 is a back plan view of the tissue distraction assembly of FIG. 1;

FIG. 5 is a plan view of the distal end of the tissue distraction assembly of FIG. 1;

FIG. 6 is a plan view of the proximal end of the tissue distraction assembly of FIG. 1;

FIG. 10 is a front plan view of the initial dilator of FIG. 8;

FIG. 11 is a cross-sectional view of the initial dilator of FIG. 8;

FIG. 12 is a perspective view of the distal end of the initial dilator of FIG. 8;

FIGS. 20-22 are perspective views of a second expander forming part of the tissue distraction assembly of FIG. 1;

DESCRIPTION OF THE PREFERRED EMBODIMENT

Figure 1:
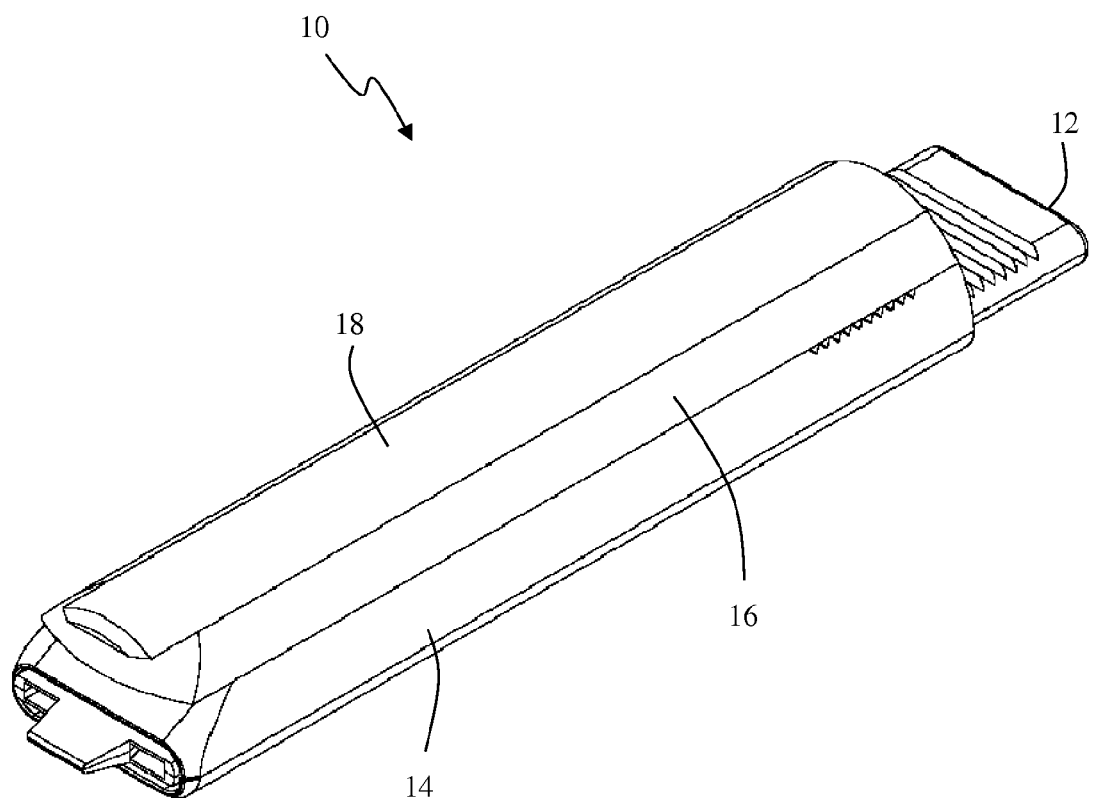
FIG. 1 is a perspective view of an example of a tissue distraction assembly according to a first embodiment of the present invention.
Figure 2:
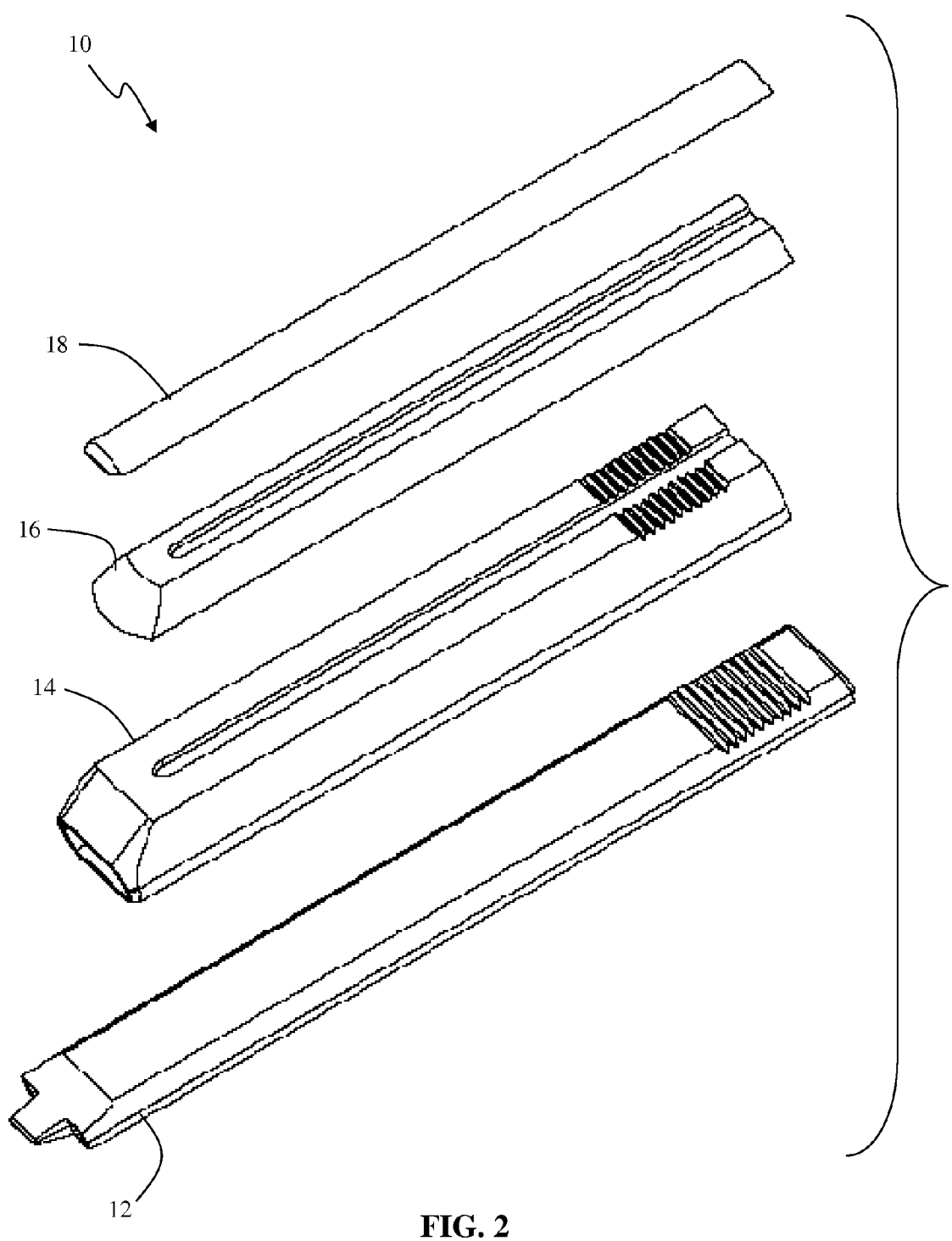
FIG. 2 is an exploded perspective view of the tissue distraction assembly of FIG. 1.
Figure 7:
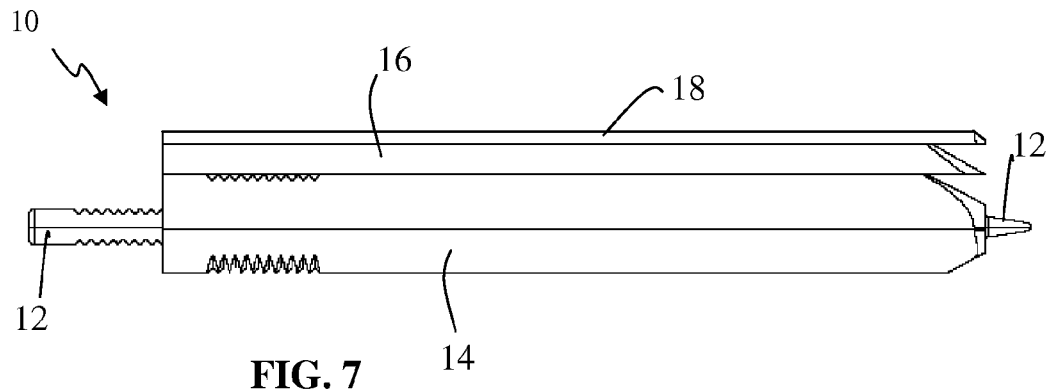
FIG. 7 is a plan view of the side of the tissue distraction assembly of FIG. 1.
Figure 8:
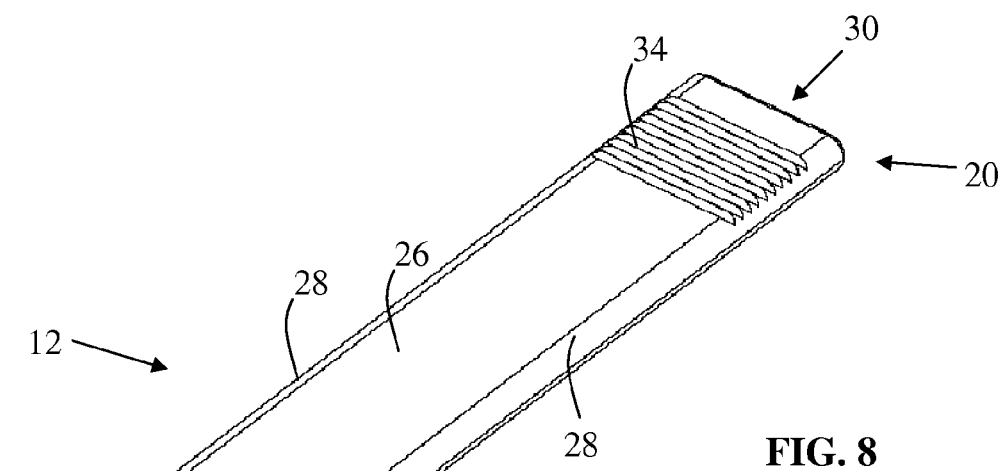
FIGS. 8 & 9 are perspective views of the an initial dilator forming part of the tissue distraction assembly of FIG. 1.
Figure 9:
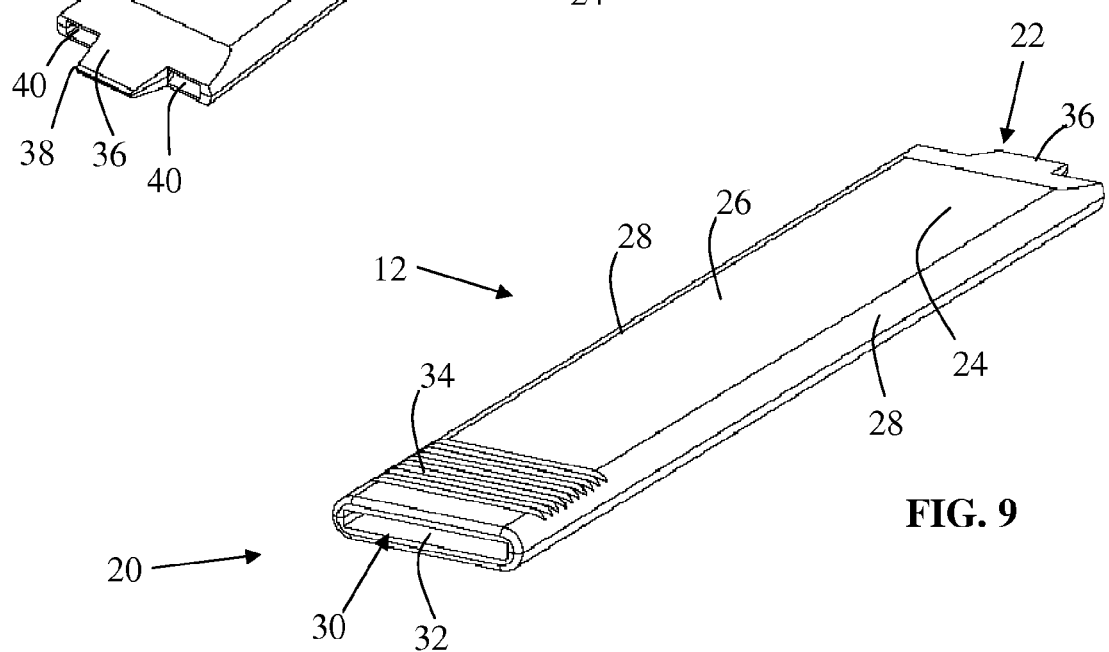
Figure 13:
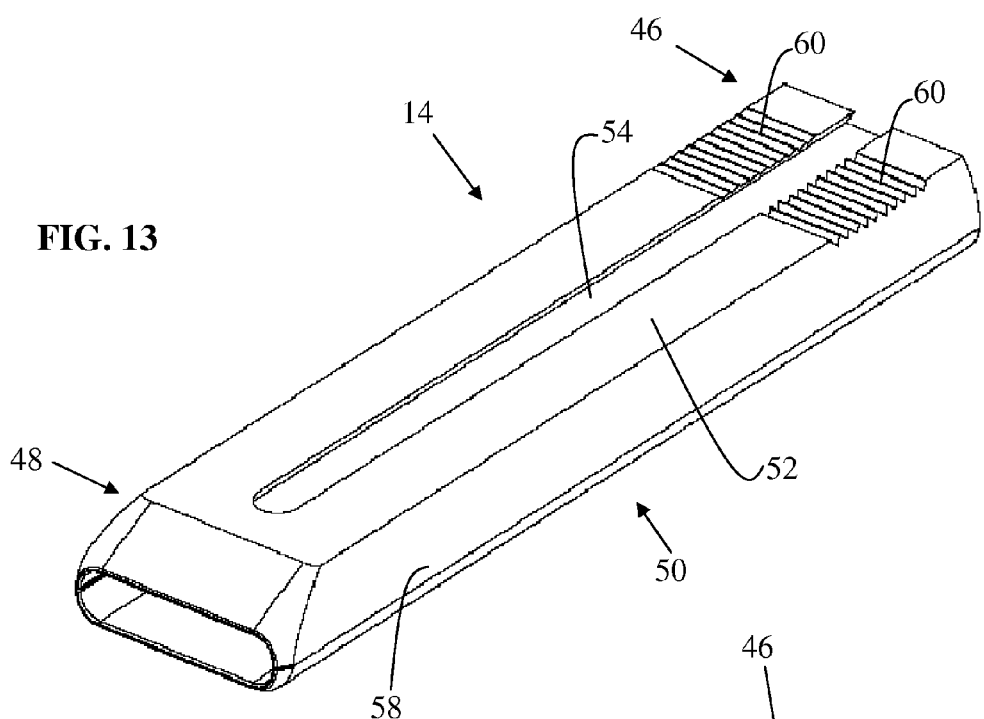
FIG. 13 is a perspective view of a secondary dilator forming part of the tissue distraction assembly of FIG. 1.
Figure 14:
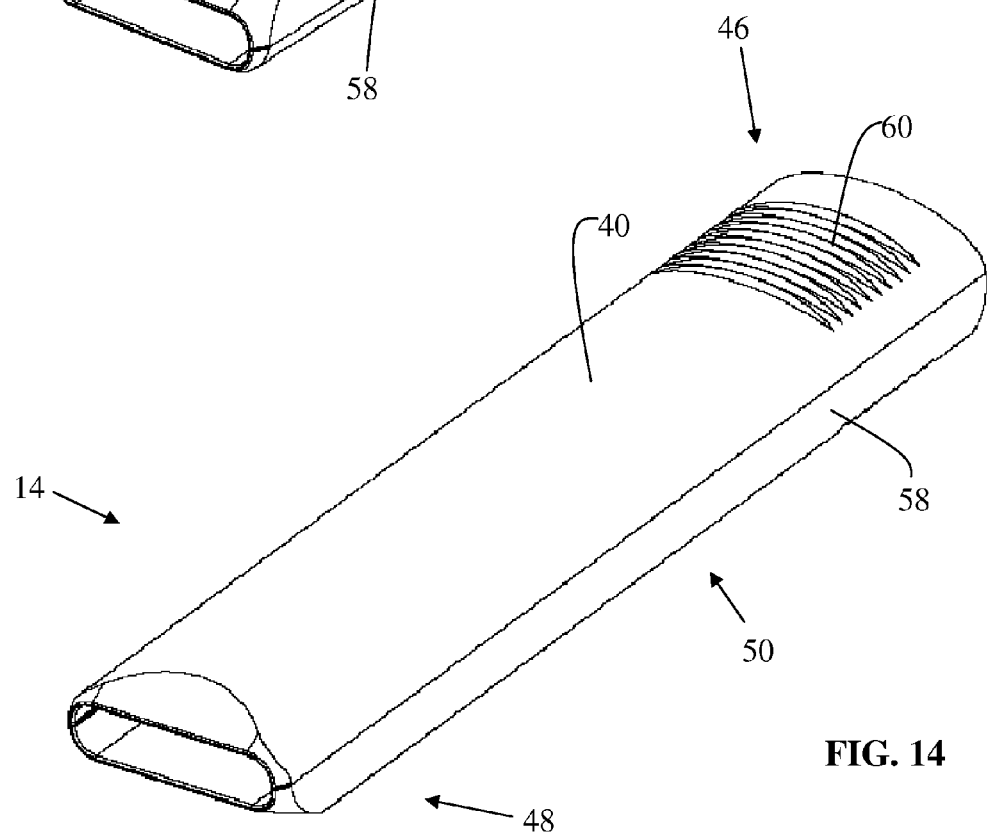
FIG. 14 is a perspective view of the secondary dilator of FIG. 13 rotated 180 degrees.
Figure 15:
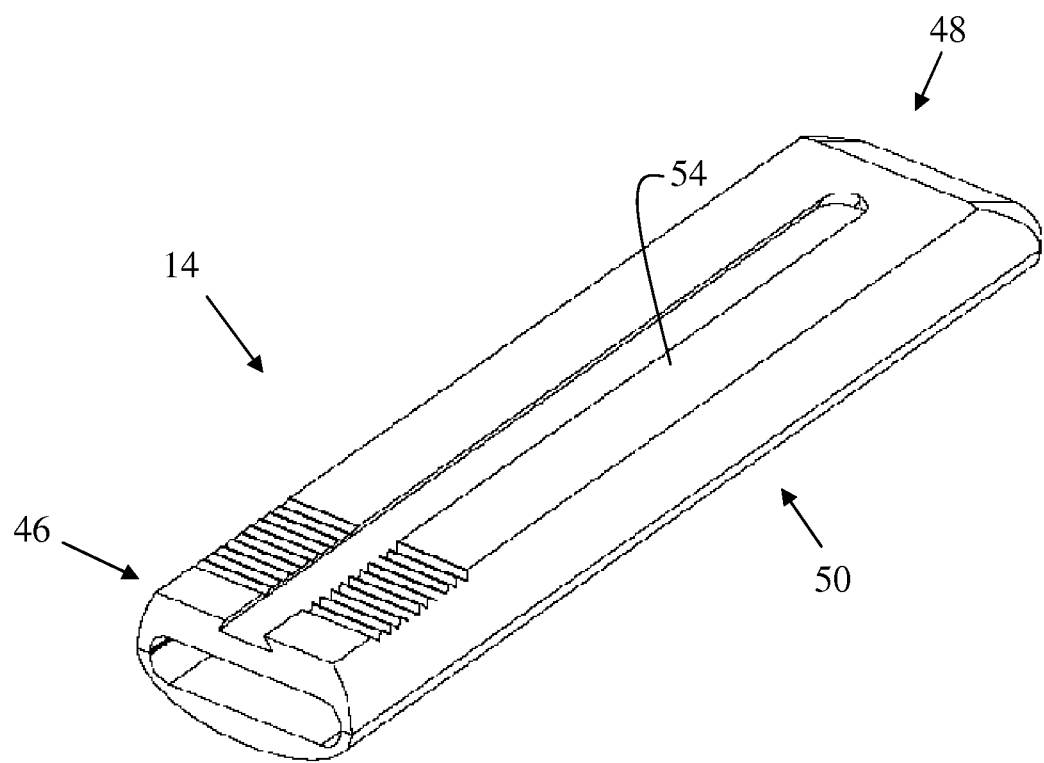
FIG. 15 is a perspective view of the secondary dilator of FIG. 13.
Figure 16:
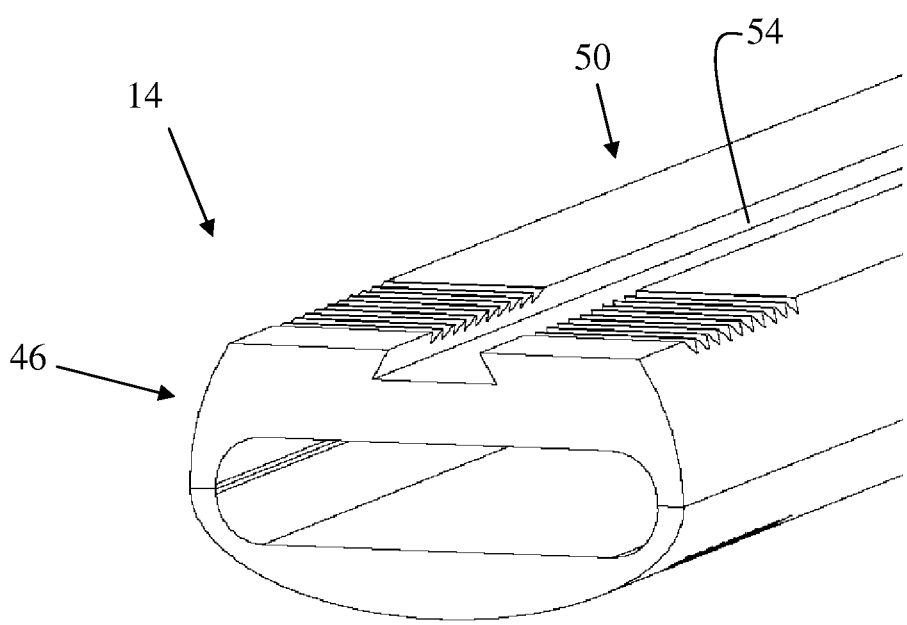
FIG. 16 is a perspective view of the proximal end of the secondary dilator of FIG. 13.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The tissue distraction system disclosed herein boasts a variety of inventive features and components that warrant patent protection, both individually and in combination.

FIGS. 1-7 illustrate an example of a tissue distraction assembly 10 according to one embodiment of the present invention. The tissue distraction assembly 10 includes a variety of sub-components dimensioned to allow for sequential dilation of a surgical tissue site in order to establish an operative corridor through a patient's skin to a surgical target site. By way of example only, the surgical target site referred to herein throughout is an intervertebral disc space situated between two adjacent vertebrae. Although particularly suited for use in lumbar spine fixation, it will be readily appreciated by those skilled in the art that the surgical fixation system of the present invention may be employed in any number of suitable orthopedic fixation approaches and procedures, including but not limited to anterior, posterior, lateral, antero-lateral, postero-lateral, cervical spine fixation, thoracic spine fixation, as well as any non-spine fixation application such as bone fracture treatment.

Tissue distraction assembly 10 includes an initial dilator 12, a secondary dilator 14, a first expander 16, and a second expander 18. The tissue distraction assembly 10 is provided with an overall generally oblong shape as opposed to a generally circular shape characterizing many of the sequential dilation systems currently available. This oblong shape serves to provide an initial distraction corridor spanning a target disc space, allowing the placement of pedicle screws at adjacent levels without additional tissue retraction. As will be explained in greater detail below, the first and second expanders 16, 18 function to bias the distraction corridor in one direction. By way of example only, based on the preferred positioning of the tissue distraction system 10 during use, the distraction corridor is biased medially (e.g. toward the patient's longitudinal midline).

Referring to FIGS. 8-12, the initial dilator 12 has a proximal portion 20, a distal portion 22, and an elongated body 24 extending therebetween. The initial dilator 12 is formed from a pair of generally planar panels 26 connected by generally curved sides 28, such that the initial dilator 12 has a generally oblong cross-section. The initial dilator 12 further has a lumen 30 extending through the dilator 12 from the proximal portion 20 to the distal portion 22. The proximal portion 20 further includes a proximal opening 32 of the lumen 30, and a plurality of friction elements 34 provided to enhance user control of the instrument. By way of example only, the friction elements 34 are provided as a plurality of ridges, however any suitable friction-inducing material and/or feature may be employed without departing from the scope of the present invention. The distal portion 22 includes a lead element 36 having a leading edge 38 extending along the lead element 36. Lead element 36 is tapered in a distal direction from the planar panels 26 to the leading edge 38 to enable the lead element 36 to advance through tissue (e.g. muscle tissue) without requiring severing or removal of that tissue. The distal portion 22 further includes a pair of distal openings 40 positioned on either side of lead element 36. Distal openings 40 represent the distal terminus of the lumen 30.

The lumen 30 extends through the initial dilator 12 from the proximal opening 32 to the distal openings 40. As shown in FIG. 11, the distal portion 22 of the initial dilator 12 further includes a wedge member 42 extending proximally into the lumen 30, effectively bifurcating the lumen 30 into a pair of distal channels 44 leading to the distal openings 40. The distal channels 44 function to guide relevant instrumentation (e.g. K-wires) into the proper positioning within the surgical target site.

Referring to FIGS. 13-16, the secondary dilator 14 has a proximal portion 46, a distal portion 48, and an elongated body 50 extending therebetween. The secondary dilator 14 includes a first side 52, a second side 56, and a pair of generally curved lateral sides 58. The first side 52 comprises a generally planar surface having an elongated recess 54 extending from the end of the proximal portion 46 substantially the length of the elongated body 50 and terminating near the distal portion 48. The second side 56 comprises a surface having a generally convex curvature. The convex surface of the second side 56 represents one boundary of the distraction corridor because any further distraction at this point will be due to the extensions 16, 18, as explained in further detail below. Both the first and second sides 52, 56 are provided with a plurality of friction elements 60 at the proximal portion 46 provided to enhance user control of the instrument. By way of example only, the friction elements 34 are provided as a plurality of ridges, however any suitable friction-inducing material and/or feature may be employed without departing from the scope of the present invention. The secondary dilator 14 further includes a lumen 62 extending through the dilator 14 from the proximal portion 46 to the distal portion 48. The lumen 62 has an oblong cross-section, and is sized and dimensioned to slideably engage the initial dilator 12. The lumen further includes a proximal opening 64 and a distal opening 66.

The distal portion 48 further includes a pair of generally planar surfaces 68, 70 that are sloped or tapered from the first and second sides 54, 56, respectively, to the distal opening 66 of the lumen 62. During tissue distraction, as the secondary dilator 14 is being advanced over the initial dilator 12 to expand the operative corridor, the tapered surfaces 68, 70 function to urge the body tissue around the path of the dilator 14. When the secondary dilator 14 has been fully inserted, the initial dilator 12 may be removed if desired, and the secondary dilator 14 may act as a stand-alone cannula.

In some instances, it may be desirable to enlarge the distraction corridor further. To achieve that end, further sequential dilators may be provided without departing from the scope of the present invention. Additionally, one or more extensions may be provided to slideably engage with the secondary dilator 14 and thereby expand the distraction corridor. The tissue distraction system 10 may be configured such that extensions are provided on one or more sides of the secondary dilator 14, to achieve a distraction corridor of any customizable shape. By way of example only, the tissue distraction assembly 10 described herein is configured to include expanders on only one side of the secondary dilator 14, creating a biased corridor configuration.

Figure 17:
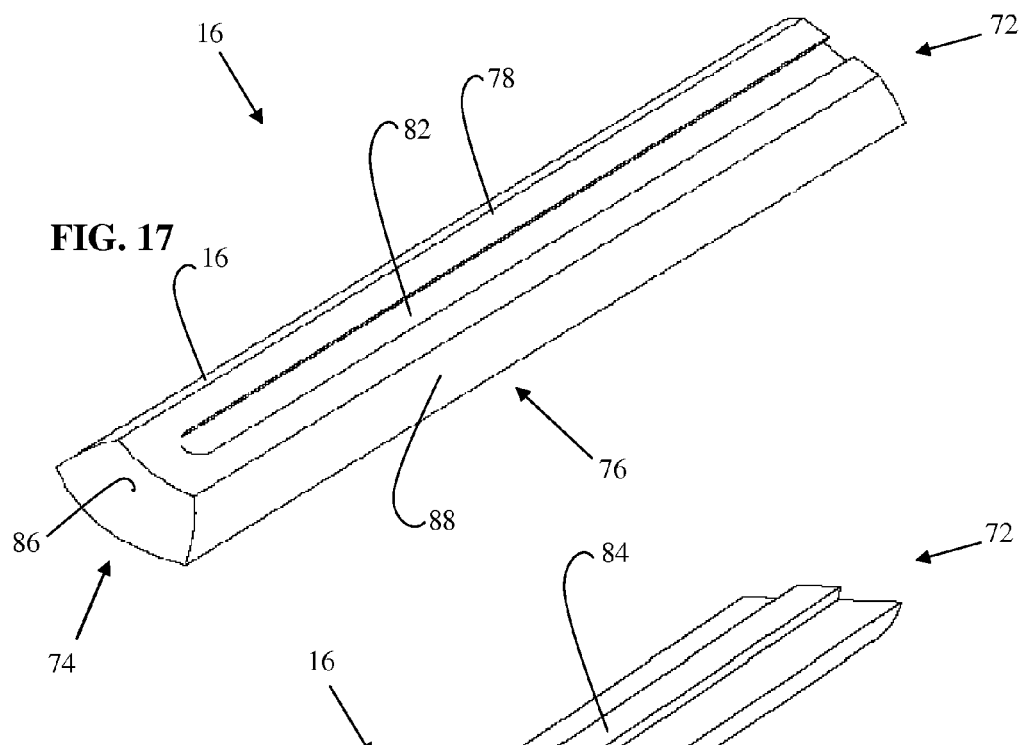
FIGS. 17-19 are perspective views of a first expander forming part of the tissue distraction assembly of FIG. 1.
Figure 18:
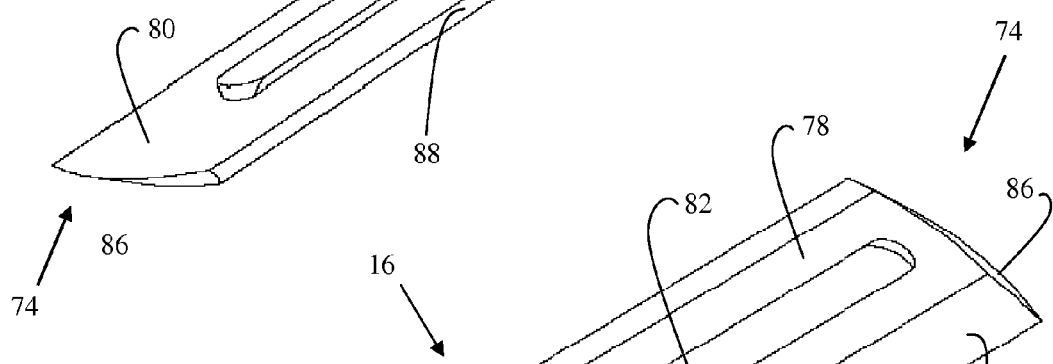
Figure 19:
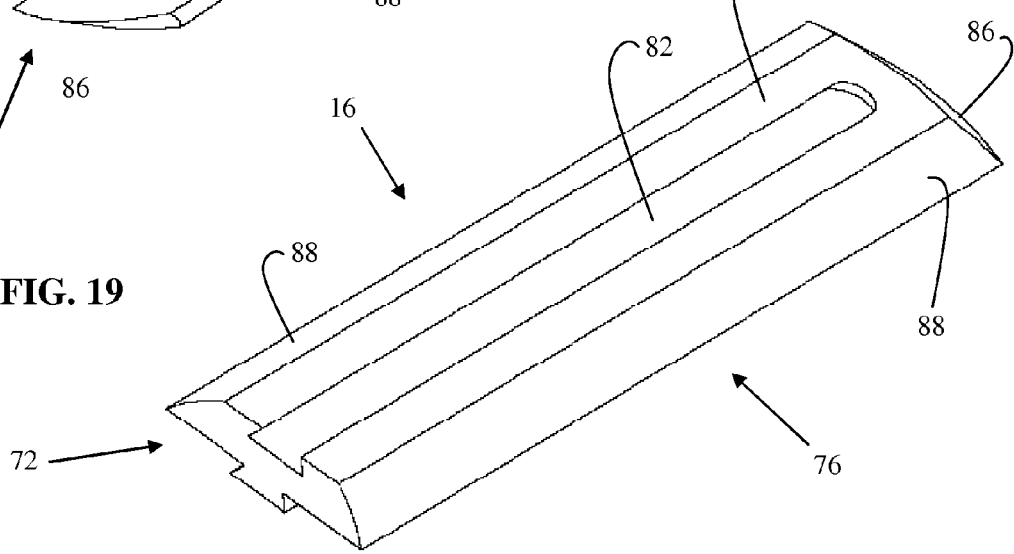

Referring to FIGS. 17-19, an example of a first expander 16 for use with the tissue distraction assembly 10 of the present invention is described. First expander 16 includes a proximal end portion 72, a distal end portion 74, and an elongated body 76 extending therebetween. The first expander 16 further includes a first side 78 comprising a generally planar surface and a second side 80 comprising a generally planar surface opposite the first side 78. The first side 78 includes an elongated recess 82 extending from the proximal end portion 72 substantially the length of the body portion 76 and terminates near the distal end portion 74. The second side 80 includes an elongated raised protrusion 84 extending from the proximal end portion 72 substantially the length of the body portion 76 and terminates near the distal end portion 74. The protrusion 84 is sized and dimensioned to slideably engage the elongated recess 54 of the secondary dilator 14. Thus, the protrusion 84 and recess 54 will have complementary shapes and sizes. Any such shape is possible, for example including but not limited to the mortise and tenon interfaces shown in the figures. The distal end portion 72 further includes a distal tapered surface 86 that slopes in a distal direction from the first surface 78 until it forms an edge with the second surface 80. The first expander 16 further includes a pair of lateral tapered surfaces 88 that slopes in a lateral direction from the first surface 78 until it forms an edge with the second surface 80. The lateral tapered surfaces 88 extend along the length of the body portion 76. Both the distal tapered surface 86 and lateral tapered surfaces 88 function to urge the body tissue around the path of the first expander 16 during tissue distraction, as the first expander 16 is being advanced over the initial dilator 12 to expand the operative corridor.

Referring to FIGS. 20-22, an example of a second expander 18 for use with the tissue distraction assembly 10 of the present invention is described. Second expander 18 includes a proximal end portion 90, a distal end portion 92, and an elongated body 94 extending therebetween. The second expander 18 further includes a first side 96 comprising a generally convex surface and a second side 98 comprising a generally planar surface opposite the first side 96. The second side 98 includes an elongated raised protrusion 100 extending from the proximal end portion 90 substantially the length of the body portion 94 and terminates near the distal end portion 92. The protrusion 100 is sized and dimensioned to slideably engage the elongated recess 82 of the first expander 16. Thus, the protrusion 100 and recess 82 will have complementary shapes and sizes. Any such shape is possible, for example including but not limited to the mortise and tenon interfaces shown in the figures. The distal end portion 92 further includes a distal tapered surface 102 that slopes in a distal direction from the first surface 96 until it forms an edge with the second surface 98. The distal tapered surface 102 functions to urge the body tissue around the path of the second expander 18 during tissue distraction, as the second expander 18 is being advanced over the first expander 16 to expand the operative corridor.

Figure 23:
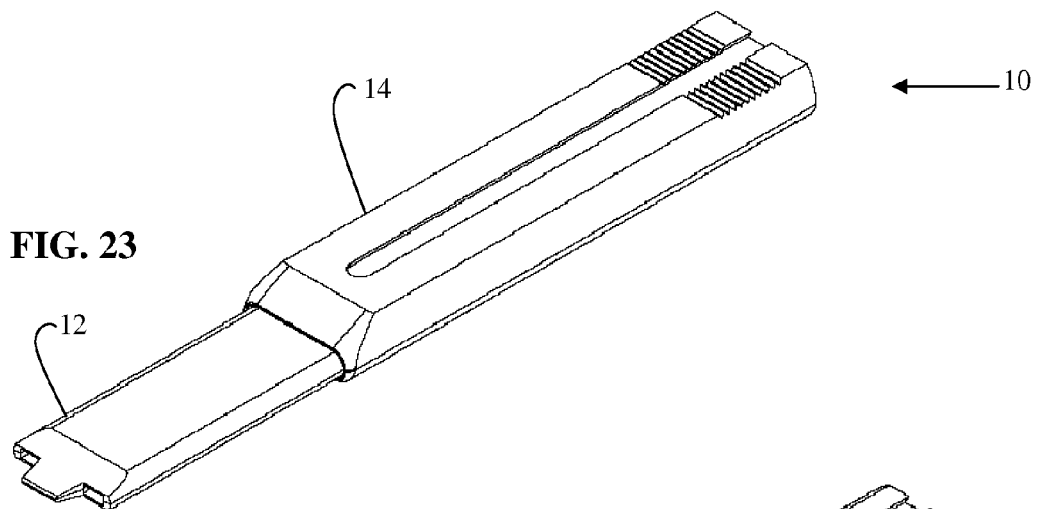
FIGS. 23-25 are perspective views of the sequential steps in a process of assembling the tissue distraction assembly of FIG. 1.
Figure 24:
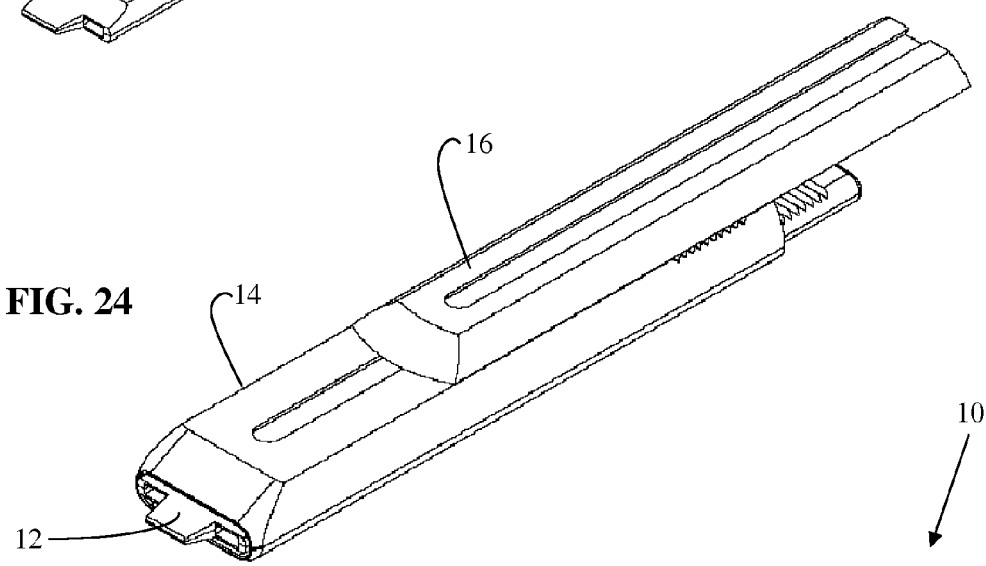
Figure 25:
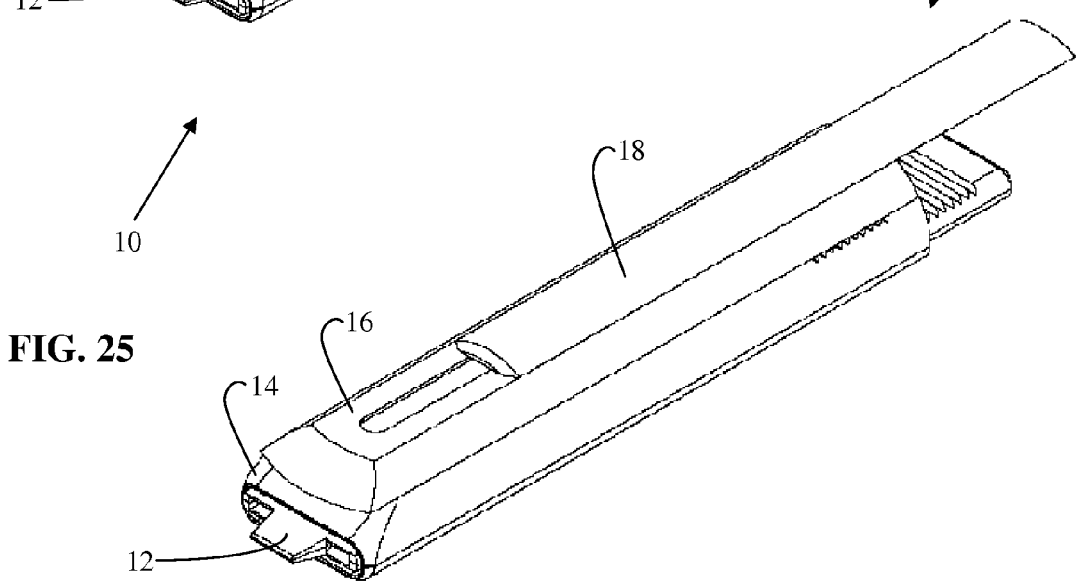

FIGS. 23-25 illustrate the sequential steps of assembling the tissue distraction assembly 10. Although not shown, the first step in the distraction process is to typically run a guide to the target site. In this instance, for example the surgeon would advance a pair of K-wires to the relevant locations (i.e. pedicles) involved in the procedure in order to guide the proper placement of the dilators. After an initial incision is made within the skin to allow passage of the dilators, the initial dilator 12 is advanced along the K-wires such that one K-wire is in each distal channel 44 of the lumen 30. Once the initial dilator 12 has been satisfactorily placed, the secondary dilator 14 is advanced over the top of the initial dilator 12 as shown in FIG. 22. If further distraction is required (e.g. medial distraction), first and second expanders 16, 18 may be employed as shown in FIGS. 23 and 24.

Figure 26:
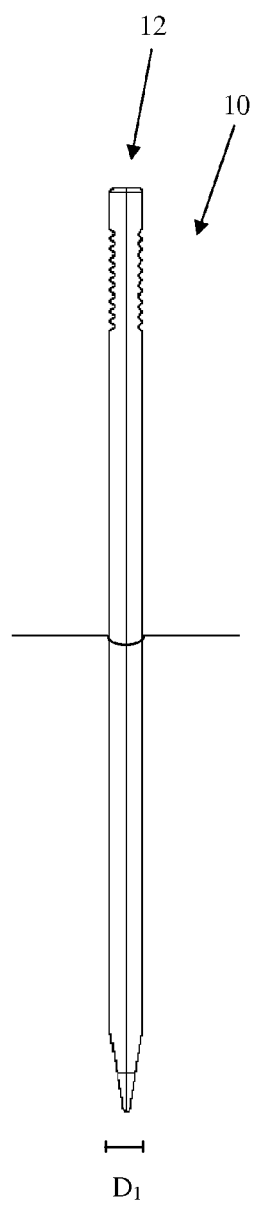
FIGS. 26-30 are plan views of the sequential steps in a process of assembling the tissue distraction assembly of FIG. 1 and in turn distracting a patient's skin tissue to establish an operative corridor according to one embodiment of the present invention.
Figure 27:
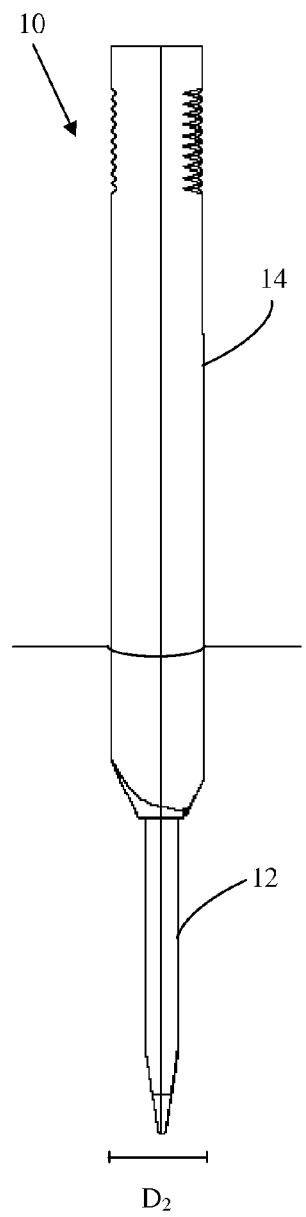
Figure 28:
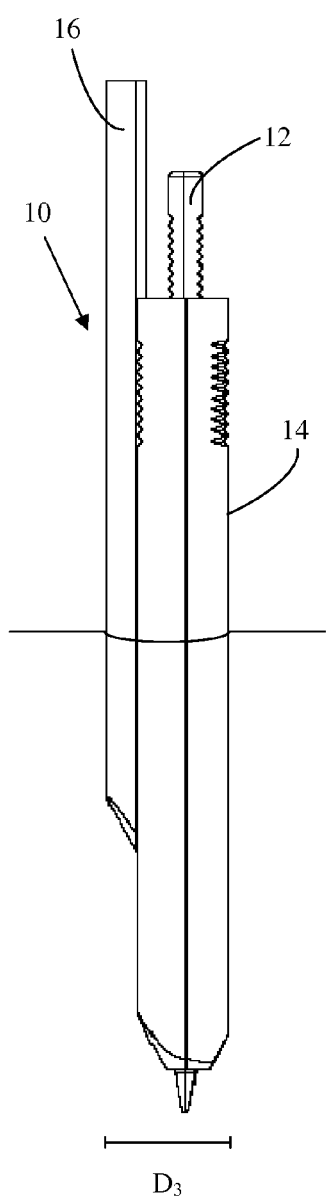
Figure 29:
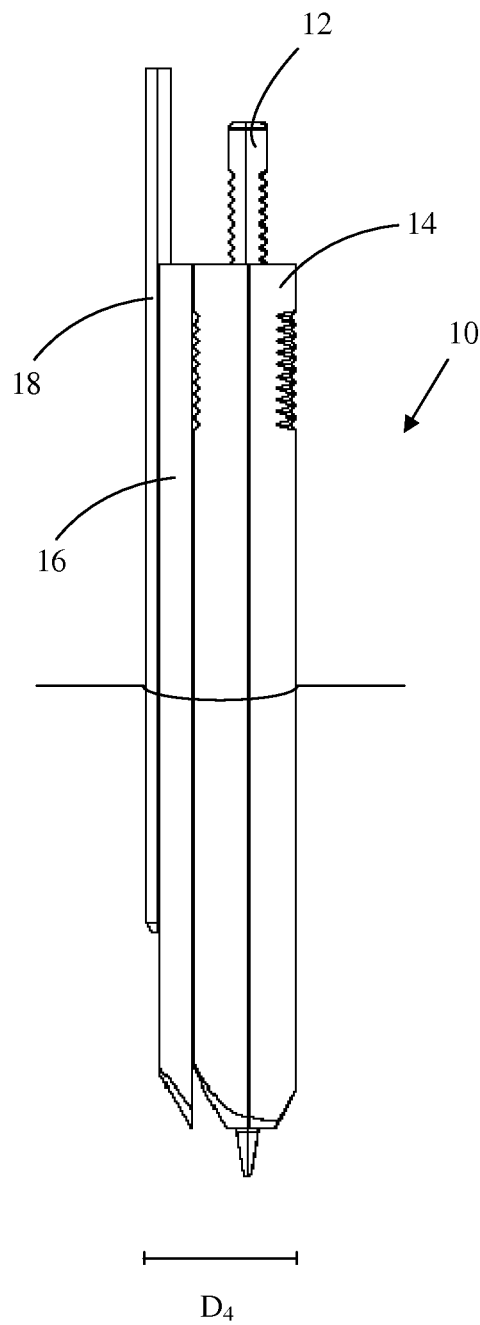
Figure 30:
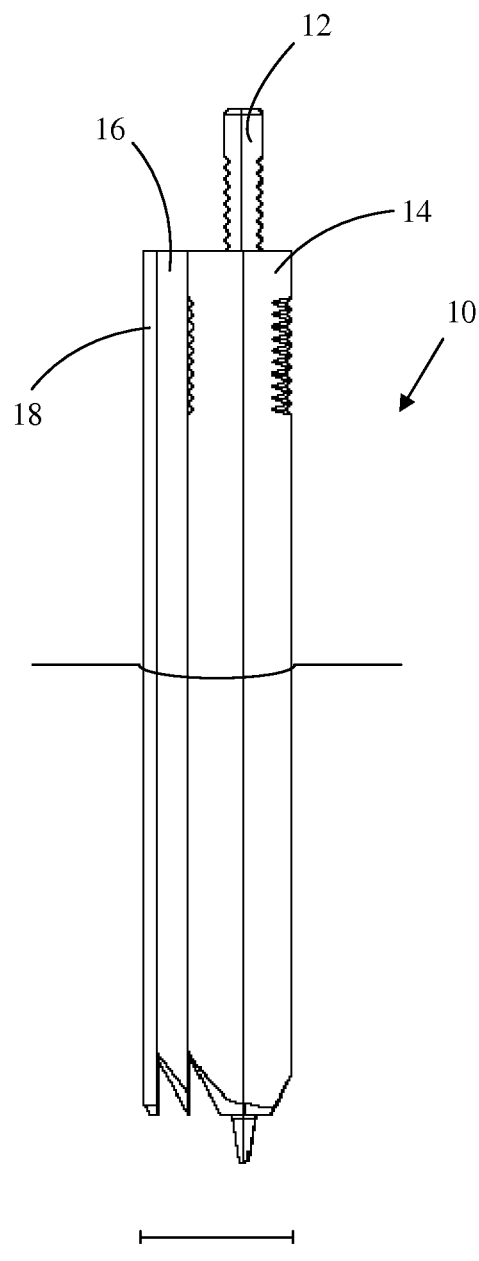

FIGS. 26-30 show the relative advantages to be gained from sequential dilation and subsequent use of expanders to bias the distraction corridor. As shown in FIG. 26, the initial dilator 12 affords a dilation distance value of $D_1$. As shown in FIG. 27, the secondary dilator 14 increases the dilation distance to $D_2$, where $D_2>D_1$. The actual distances involved are customizable depending upon the needs of the surgeon. To increase the distances, one need only to use a wider dilator (either initial dilator 12 or secondary dilator 14). FIG. 27 illustrates the addition of first expander 16 to the tissue distraction assembly 10. The first expander 16 increases the dilation distance to $D_3$, where $D_3>D_2$. However, due to the first expander 16 being used on only one side of the secondary dilator 14, the increased distraction is asymmetrical. FIG. 28 illustrates the addition of second expander 18 to the tissue distraction assembly 10. The second expander 18 increases the dilation distance to $D_4$, where $D_4>D_3$. As with the first expander 16, the second expander 18 asymmetrically increases the distraction corridor.

Once the distraction corridor has been created, a tissue retractor may be advanced to the spine over the distraction assembly (not shown). The distraction assembly may be removed and the retractor may be operated to expand to establish an operative corridor. With the operative corridor established, the surgeon may proceed with the desired procedure, for example, a transforaminal lumbar interbody fusion (TLIF) spinal procedure. This procedure continues with a facetectomy in which at least a portion of the facet joint is removed, allowing access to the intervertebral disc space. The disc space is prepared using techniques generally known in the art, including disc brushes, scrapers, etc. The interbody implant is then inserted into the cleaned out disc space. The retractor may then be removed from the patient, closing the operative corridor. The surgeon will then close the operative wound, completing the procedure.

While this invention has been described in terms of a best mode for achieving this invention's objectives, it will be appreciated by those skilled in the art that variations may be accomplished in view of these teachings without deviating from the spirit or scope of the invention.

What is claimed is:

1. A sequential dilation system, comprising:
   a first cannula having a first wall, a second wall, and opposing sidewalls each extending from a proximal end to a distal end and together having an oblong cross-section, the first cannula further having a first lumen extending from sidewall to sidewall and from the proximal end to the distal end, wherein the distal end of the first cannula includes a wedge, the distal end of the wedge comprising extensions of the first and second walls such that the first cannula has a first length dimension at a center that is greater than a second length dimension adjacent the sidewalls, the proximal end of the wedge having a pair of convergent tapered surfaces extending proximally into the first lumen and intersecting at an edge, thereby bifurcating the first lumen into a pair of distal channels at the distal end; and a second cannula having a first wall, a second wall, and opposing sidewalls each extending from a proximal end to a distal end, and a lumen extending from sidewall to sidewall and from the proximal end to the distal end and a second lumen extending longitudinally therethrough, the second lumen having a length dimension, a width dimension, and an oblong cross-section taken across the width dimension, the second lumen dimensioned to slideably receive the first cannula therein.

2. The sequential dilation system of claim 1, wherein the first cannula further comprises a pair of apertures at the distal end, the apertures in communication with the first lumen.

3. The sequential dilation system of claim 1, wherein the second cannula has a first outer surface and a second outer surface opposite the first outer surface, wherein the first outer surface is curved and the second outer surface is planar.

4. The sequential dilation system of claim 3, further comprising a first width extender configured to mate with the second cannula at the second surface to expand the width of the assembled sequential dilation system.

5. The sequential dilation system of claim 4, further comprising a second width extender configured to mate with the first width extender to expand the width of the assembled sequential dilation system.

6. A sequential dilation system, comprising:

a first cannula having a first wall, a second wall, and opposing sidewalls each extending from a proximal end to a distal end and together having an oblong cross-section, the first cannula further having a first lumen extending from sidewall to sidewall and from the proximal end to the distal end, the first cannula further having a pair of distal openings at the distal end, the first cannula further having a lead element between the distal openings, wherein the lead element is tapered in a distal direction from the first and second walls of the first cannula; and a second cannula having a first wall, a second Wall, and opposing sidewalls each extending from a proximal end to a distal end and a lumen extending from sidewall to sidewall and from the proximal end to the distal end, the lumen dimensioned to pass the first cannula therethrough, the first wall having a curved outer surface and the second wall having a planar outer surface.

7. The sequential dilation system of claim 6, comprising a first width extender configured to slideably mate with the second planar wall of the second cannula and expand the width of the assembled sequential dilation system in a single direction.

8. The sequential dilation system of claim 6, further comprising a second width extender configured to mate with the first width extender to further expand the width of the assembled sequential dilation system in the single direction.

9. A sequential dilation system, comprising:

a first cannula having a first wall, a second wall, and opposing sidewalls each extending from a proximal end to a distal end and together having an oblong cross-section, the first cannula further having a first lumen extending from sidewall to sidewall and from the proximal end to the distal end; and a second cannula having a first wall, a second wall, and opposing sidewalls each extending from a proximal end to a distal end and a lumen extending from sidewall to sidewall and from the proximal end to the distal end, the lumen dimensioned to pass the first cannula therethrough, the first wall having a curved outer surface and the second wall having a planar outer surface, the second wall planar outer surface having an elongate engagement feature extending from the proximal end towards the distal end.

10. The sequential dilation system of claim 9, wherein the elongate engagement feature is a recess extending through the proximal end towards the distal end.

11. The sequential dilation system of claim 9, further comprising a first expander having an elongate raised protrusion that is configured and dimensioned to engage the elongate engagement feature.

12. The sequential dilation system of claim 9, further comprising a first expander having a first side with a recess therein and a second side with a protrusion thereon, wherein the second side of the first expander is configured to mate with the second wall of the second cannula.

13. The sequential dilation system of claim 9, further comprising:

a first expander having a first side and a second side, wherein the second side of the first expander is mateable with the second wall of the second cannula; and a second expander mateable with the first side of the first expander.

14. The sequential dilation system of claim 9, further comprising:

a first expander having an elongate recess extending from a proximal end towards a distal end of the first expander, wherein the first expander is mateable with the second wall of the second cannula; and a second expander having an elongate raised protrusion that is configured and dimensioned to engage the elongate recess.

* * * * *